United States Patent
Aribert et al.

(10) Patent No.: US 9,902,663 B2
(45) Date of Patent: *Feb. 27, 2018

(54) METHOD FOR DEHYDRATING A MIXTURE CONTAINING ETHANOL AND ISOPROPANOL

(71) Applicants: IFP Energies nouvelles, Rueil-Malmaison (FR); TOTAL RESEARCH & TECHNOLOGY FELUY, Seneffe (BE)

(72) Inventors: Nicolas Aribert, Moirans (FR); Laure Brandhorst, Lyons (FR); Vincent Coupard, Villeurbanne (FR); Sylvie Maury, Saint Maurice d'Argoire (FR); Tom Vivien, Lyons (FR)

(73) Assignees: IFP Energies nouvelles, Rueil-Malmaison (FR); TOTAL RESEARCH & TECHNOLOGY FELUY, Seneffe (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/039,613

(22) PCT Filed: Oct. 8, 2014

(86) PCT No.: PCT/EP2014/071550
§ 371 (c)(1),
(2) Date: May 26, 2016

(87) PCT Pub. No.: WO2015/078624
PCT Pub. Date: Jun. 4, 2015

(65) Prior Publication Data
US 2017/0022124 A1    Jan. 26, 2017

(30) Foreign Application Priority Data

Nov. 27, 2013 (FR) ..................... 13 61684

(51) Int. Cl.
*C07C 1/24* (2006.01)
*B01J 21/04* (2006.01)
*B01J 35/10* (2006.01)

(52) U.S. Cl.
CPC ............... *C07C 1/24* (2013.01); *B01J 21/04* (2013.01); *B01J 35/1019* (2013.01); *B01J 35/1061* (2013.01); *C07C 2521/04* (2013.01); *Y02P 20/52* (2015.11)

(58) Field of Classification Search
CPC ......... C07C 1/24; C07C 29/149; C07C 67/08; C07C 11/04; C07C 11/06; C07C 31/08; C07C 31/10; C07C 69/24; C07C 2521/04; B01J 21/04; B01J 35/1019; B01J 35/1061
USPC ........................................ 585/638, 639, 640
See application file for complete search history.

(56) References Cited

U.S. PATENT DOCUMENTS

| 5,475,183 | A | 12/1995 | Araki et al. |
| 9,249,066 | B2 * | 2/2016 | Minoux .................... C07C 1/24 |
| 2011/0172475 | A1 | 7/2011 | Peters et al. |

FOREIGN PATENT DOCUMENTS

| EP | 0379803 A1 | 8/1990 | |
| EP | 0498573 A1 | 8/1992 | |
| WO | WO 2004078336 A2 * | 9/2004 | ............... C07C 1/24 |
| WO | 2011162717 A1 | 12/2011 | |
| WO | WO 2011162717 A1 * | 12/2011 | ............ B01J 21/066 |

OTHER PUBLICATIONS

International Search Report for PCT/EP2014/071550 dated Jan. 21, 2015.

* cited by examiner

*Primary Examiner* — Sharon Pregler
(74) *Attorney, Agent, or Firm* — Millen White Zelano & Branigan, PC (57) ABSTRACT

Production of a mixture of ethylene and propylene from a mixture containing ethanol and isopropanol and having a water content between 30 and 75 wt. % is obtained by a process comprising:
a) contacting the mixture in a dehydration unit with a dehydration catalyst chosen from:
   an alumina (A) having a BET specific surface area between 200 and 350 m²/g, a mean mesopore diameter between 5 and 15 nm, a sodium content of less than 50 ppm by weight, and a sulphur content of less than 40 ppm by weight; and
   an alumina (B) having a BET specific surface area between 130 and 180 m²/g, a mean mesopore diameter between 14 and 20 nm, a sodium content between 300 and 600 ppm by weight, and a sulphur content between 800 and 1300 ppm by weight;
b) withdrawing an effluent containing ethylene and propylene from the dehydration unit.

22 Claims, 3 Drawing Sheets

METHOD FOR DEHYDRATING A MIXTURE CONTAINING ETHANOL AND ISOPROPANOL

The present invention relates to a process for the production of a mixture of ethylene and propylene from an aqueous mixture containing ethanol and isopropanol. The process according to the invention allows in particular the treatment of an aqueous mixture of ethanol and isopropanol which is obtained by an IBE (Isopropanol-Butanol-Ethanol) type fermentation of sugars.

STATE OF THE ART

The light olefins are important intermediates in the chemical industry and are mainly produced by catalytic cracking or steam cracking of hydrocarbons.

For example propylene is widely used in the chemical industry in the production of acrylonitrile, acrylic acid and above all polypropylene. The same applies to ethylene which is used for the synthesis of a large number of polymers and plastic materials, such as polyvinyl chloride (PVC) and polyethylene (PE).

In order to respond to future challenges associated with decreasing oil resources and environmental concerns, much research is currently being carried out in order to develop alternative technologies for the syntheses of these intermediates from renewable resources.

At present one of the most studied routes for the production of olefins is that of the catalytic dehydration of alcohols.

The dehydration reaction of ethanol to ethylene is known and has been presented in detail since the end of the $19^{th}$ century. It is known that this reaction is very endothermic, balanced and shifted toward ethylene at high temperature. The reference catalyst that is often used is a monofunctional acid catalyst. Gamma-alumina is the most cited catalyst. The article "*The Dehydration of Alcohols over Alumina. I: The reaction scheme*", H. Knözinger, R. Köhne, *Journal of Catalysis* (1966), 5, 264-270 is considered to be the basic publication on the works on the dehydration of alcohols including ethanol.

The zeolites are also used for this application, and in particular ZSM5 since the 1980s, as described in "*Reactions of ethanol over ZSM-5*", S. N. Chaudhuri & al., *Journal of Molecular Catalysis* 62:289-295 (1990).

The dehydration route for alcohols corresponds well to the problem of producing olefins in an alternative and "green" manner. In fact, ethanol can be synthesized by the fermentation of sugars obtained from renewable sources such as starch- or sugar-containing plants (e.g. maize, sugar cane respectively) or from lignocellulosic biomass such as for example wood shavings or culture residues (wheat straw). Document WO 2004/078336 is known from the state of the art, which discloses a process for the production of α-olefins by dehydration of linear or branched alcohols having 4 to 14 carbon atoms in the presence of a γ alumina comprising:

- a pore volume greater than 0.9 mL/g (determined according to the DIN 66133 method);
- pores in the mesoporous domain (maximum diameter comprised between 20 and 90 Å);
- pores in the macroporous domain (maximum diameter greater than 250 Å).

The subject of application WO 2011/162717 is a process for the production of olefins by dehydration of a mixture of alcohols using a catalyst comprising a zeolite doped with a metallic element chosen from: Mg, Ca, Ba, Sr, Cr, Mn, Fe, Co, Ni, Cu, Zn, Ga, Ce, Ag, Bi, Ti, V, Zr, Mo, W, Li, La. The use of alcohols obtained by the treatment of biomass is envisaged in this document.

Finally, the patent application FR 2 961 202 describes a process for the production of C4 olefins from a C4 mono-alcohol feedstock by a dehydration reaction of said alcohol in the presence of a catalyst based on alumina with controlled porosity.

A purpose of the present invention is to provide a process for the production of a mixture of ethylene and propylene directly from a mixture containing water, ethanol and isopropanol. According to the invention, the process applies in particular to a mixture of ethanol and isopropanol of biological origin obtained from the treatment of biomass.

SUMMARY OF THE INVENTION

Therefore the present invention relates to a process for the production of a mixture of ethylene and propylene from a mixture containing ethanol and isopropanol and having a water content comprised between 30 and 75% by weight with respect to the total weight of the mixture, in which:

a) the mixture is brought into contact, in a dehydration unit, with a dehydration catalyst chosen from:
  - an alumina (A) having a BET specific surface area measured according to the standard ASTM D 3663-03 comprised between 200 and 350 m$^2$/g, a mean mesopore diameter comprised between 5 and 15 nm, a sodium content of less than 50 ppm by weight and a sulphur content of less than 40 ppm by weight; and
  - an alumina (B) having a BET specific surface area measured according to the standard ASTM D 3663-03 comprised between 130 and 180 m$^2$/g, a mean mesopore diameter comprised between 14 and 20 nm, a sodium content comprised between 300 and 600 ppm by weight and a sulphur content comprised between 800 and 1300 ppm by weight;

the bringing into contact being carried out at a temperature comprised between 350 and 500° C., at a total pressure comprised between 0.2 and 2 MPa and with a weight hourly space velocity (whsv) defined as being the ratio of the mass flow rate of ethanol and isopropanol to the mass of catalyst comprised between 1 and 10 h$^{-1}$ b) an effluent containing ethylene and propylene is drawn off from said dehydration unit.

The process according to the invention thus makes it possible to respond to the challenges of the energy transition by proposing an alternative process to the petrochemical sector for the production of ethylene and propylene, starting from a mixture of alcohols which can be of biological origin.

Surprisingly, the inventors have found that a catalyst having the characteristics mentioned above has a high dehydration activity, while also being selective for the sought olefins.

The process according to the invention has the advantage that it dispenses with a stage of separating the ethanol from the isopropanol before the dehydration stage. In fact, thanks to the catalysts according to the invention, it is possible, in a single catalytic stage, to dehydrate the mixture of said alcohols and thus produce an effluent comprising ethylene and propylene.

The process is therefore advantageous from an economic and energy point of view when it is envisaged to produce ethylene and propylene for petrochemistry. In fact, thanks to the process it is not necessary to carry out a prior separation of the ethanol and the isopropanol from the aqueous mixture before dehydration. This separation of the two alcohols is particularly costly in terms of investment because in order to be efficient, due to the existence of azeotropic compositions, it is necessary not only to concentrate the mixture of alcohols in such a way as to obtain a concentration of alcohols greater than 50% by weight, but also to utilize a distillation column having a large number of trays. Thus an advantage of the process according to the invention is that it makes it possible to produce ethylene and propylene for petrochemistry involving a smaller number of unit operations which produces a not inconsiderable economic advantage. Thus, after the dehydration stage according to the invention, a flow is obtained containing propylene and ethylene which can, however, be easily separated by distillation.

The process according to the invention makes it possible to dehydrate a mixture containing water, ethanol and isopropanol and to advantageously use the water contained in said mixture as thermal fluid during the dehydration stage. The dehydration reaction is highly endothermic and the fact that the feedstock is diluted with water makes it possible to reduce the endothermic nature of the reaction and thus carry out the reaction with a limited number of reactors. The water also makes it possible, thanks to the feedstock/effluent exchangers, to recover the condensation energy of the reaction products in order to produce the temperature required to dehydrate the feedstock.

Preferably, the alumina (A) has a BET specific surface area measured according to the standard ASTM D 3663-03 comprised between 200 and 280 $m^2/g$ and more preferably comprised between 200 and 230 $m^2/g$.

Preferably the alumina (A) has a mean mesopore diameter comprised between 6 and 12 nm and more preferably comprised between 7 and 11 nm.

Preferably, the alumina (B) has a BET specific surface area measured according to the standard ASTM D 3663-03 comprised between 150 and 180 $m^2/g$.

Preferably the alumina (B) has a mean mesopore diameter comprised between 15 and 20 nm.

According to a very preferred embodiment, the catalysts (A) and (B) according to the invention are gamma aluminas. More preferably, the catalysts according to the invention are constituted by gamma alumina.

The aluminas according to the invention can be prepared by any method known to a person skilled in the art. For example they can be obtained from an alumina gel (or gel of alumina) which essentially comprises a precursor of the aluminium oxy(hydroxide) (AlO(OH)) type—also denoted boehmite. The alumina gel (otherwise denoted boehmite gel) is for example synthesized by precipitation of basic and/or acid solutions of aluminium salts induced by changing the pH or any other method known to a person skilled in the art (P. Euzen, P. Raybaud, X. Krokidis, H. Toulhoat, J. L. Le Loarer, J. P. Jolivet, C. Froidefond, Alumina, in Handbook of Porous Solids, Eds F. Schüth, K. S. W. Sing, J. Weitkamp, Wiley-VCH, Weinheim, Germany, 2002, pp. 1591-1677). The gel obtained is then subjected to one or more heat treatment stages which comprise in particular drying and calcination in order to form an alumina having the required structural characteristics according to the invention. It should be noted that the aluminas according to the invention can also be obtained from other alumina precursors such as for example bauxite, bayerite or by the oxidation of aluminium.

According to a particular embodiment, when the mixture also contains n-butanol, a stage of separating the butanol is carried out before stage a), which consists for example of sending said mixture into a distillation column from where an effluent containing water, ethanol and isopropanol is drawn off at the top of the column and an effluent containing butanol is drawn off at the bottom. The effluent containing water, ethanol and isopropanol is then treated in the dehydration unit according to stage a) of the process.

According to a particular embodiment, before stage a), a stage of reducing the water content (drying stage) of the ethanol-isopropanol-water mixture is carried out which comprises bringing the mixture into contact, in a liquid-liquid extraction column, with an aromatic cut comprising a mixture of aromatic compounds having 7 to 10 carbon atoms. The aromatic cut is preferably a mixture of 1,3,5-trimethylbenzene and 1,2,4-trimethylbenzene. Alternatively, the aromatic cut is a heavy reformate cut originating from a separation of the reforming product of a gasoline cut. The bringing into contact of the mixture of alcohols with the aromatic cut in the extraction column is preferably carried out in counter-current and preferably with a contact temperature comprised between 70 and 90° C.

This extraction stage makes it possible to separate an aqueous fraction and an organic fraction containing the aromatic cut, ethanol, isopropanol, optionally butanol and traces of water from the column. The organic fraction is then sent into a distillation column configured in order to separate an effluent containing the aromatic cut and an effluent containing ethanol, isopropanol and optionally butanol. Finally the effluent containing ethanol and isopropanol is sent into the dehydration unit of stage a). If the effluent containing the mixture of ethanol and isopropanol also comprises butanol, a stage of separating the butanol from the effluent is preferably carried out before the dehydration stage.

Alternatively, before stage a), a stage of reducing of the water content of the ethanol-isopropanol-water mixture is carried out, which consists of sending the mixture into a distillation column in order to separate an aqueous fraction and an effluent having a reduced water content and containing ethanol and isopropanol. The effluent thus recovered is treated in the dehydration unit according to stage a). If the effluent containing the mixture of ethanol and isopropanol also comprises butanol, a stage of separating the butanol from the effluent is carried out before the dehydration stage.

Preferably, the mixture containing ethanol and isopropanol originates from an Isopropanol-Butanol-Ethanol (IBE) fermentation unit for sugars which are obtained by the treatment of biomass, for example lignocellulosic biomass.

Preferably, the process is carried out in two adiabatic reactors in series.

DETAILED DESCRIPTION OF THE INVENTION

The feedstock treated in the process according to the invention is a mixture containing between 30 and 75% by weight of water with respect to the total weight of the mixture of ethanol and isopropanol. The mixture which is treated by dehydration according to the invention can comprise any proportion of ethanol and isopropanol. Preferably, the mixture contains between 1 and 75% by weight of ethanol and between 99 and 25% by weight of isopropanol with respect to the total weight of ethanol and isopropanol. Very preferably, the mixture contains at least 25% by weight of ethanol and at least 75% by weight of isopropanol.

The feedstock can advantageously come from non-fossil resources. Preferably the feedstock is a product originating from the biological treatment of biomass. Preferably, the ethanol/isopropanol feedstock is a feedstock produced by an IBE type fermentation of sugars originating for example from the cultures of sugar-containing plants such as sugar cane (saccharose, glucose, fructose, and sucrose), sugar beet, or also starch-containing plants (starch) or lignocellulosic biomass or hydrolyzed cellulose (mainly glucose and xylose, galactose).

According to the invention the conversion of ethanol and isopropanol to ethylene and propylene respectively is carried out, for example in a reactor, by bringing the feedstock into contact with a catalyst chosen from:

an alumina (A) having a BET specific surface area measured according to the standard ASTM D 3663-03 comprised between 200 and 350 $m^2/g$, a mean mesopore diameter comprised between 5 and 15 nm, a sodium content of less than 50 ppm by weight and a sulphur content of less than 40 ppm by weight; and an alumina (B) having a BET specific surface area measured according to the standard ASTM D 3663-03 comprised between 130 and 180 $m^2/g$, a mean mesopore diameter comprised between 14 and 20 nm, a sodium content comprised between 300 and 600 ppm by weight and a sulphur content comprised between 800 and 1300 ppm by weight.

Determination of the mean mesopore diameter is carried out by mercury porosimetry according to the standard ASTM D 4284-03 with a contact angle of 140°. Analysis by mercury porosimetry corresponds to the intrusion of a volume of mercury characteristic of the existence of mesopores and macropores in said catalyst according to standard ASTM D4284-03, it being assumed that the pores are of cylindrical shape. This technique provides the value of the mesoporous mercury volume, defined as being the volume of mercury adsorbed by all of the pores having a diameter in the mesopore range, namely comprised between 2 and 50 nm. This mean mesopore diameter is obtained from the derived curve dV/d log(D) (V being the volume of mercury adsorbed and D the diameter of the pores) as a function of the diameter of the pores D and corresponds to the ordinate for which the abscissa dV/d log(D) is at its maximum.

The dehydration catalyst used in stage a) of the process according to the invention is advantageously formed in the form of grains of different shapes and sizes. It is advantageously used in the form of cylindrical or multilobed extrudates, such as bilobed, trilobed, multilobed of straight or twisted shape, but can optionally be manufactured and used in the form of crushed powder, pellets, rings, beads, wheels, or spheres. Preferably, said catalyst is in the form of extrudates.

Said dehydration catalyst used in stage a) of the process according to the invention is advantageously utilized in at least one reactor, in a fixed bed or in a moving bed. Within the scope of the invention, the catalyst can include at least at least one matrix of the oxide type, also called binder. Said matrix is advantageously selected from the elements of the group formed by clays (such as for example from the natural clays such as kaolin or bentonite), magnesia, aluminas, silicas, silica-aluminas, aluminates, titanium oxide, boron oxide, zirconia, aluminium phosphates, titanium phosphates, zirconium phosphates, and carbon.

According to a preferred embodiment, the alumina denoted "A" has a BET specific surface area measured according to the standard ASTM D 3663-03 comprised between 200 and 280 $m^2/g$ and preferably between 200 and 230 $m^2/g$. Preferably, the alumina denoted "A" has a mean mesopore diameter comprised between 6 and 12 nm and more preferably comprised between 7 and 11 nm.

According to another embodiment, the alumina denoted "B" has a BET specific surface area measured according to the standard ASTM D 3663-03 comprised between 150 and 180 $m^2/g$. Preferably, the alumina denoted "B" has a mean mesopore diameter comprised between 15 and 20 nm.

Preferably, before being utilized, the catalysts according to the invention are subjected to a calcination stage which has the objective of removing the species optionally adsorbed onto their surface.

The calcination stage consists for example of heating the catalyst to a temperature of at least 500° C. under a flow of air or nitrogen for at least 1 hour.

The dehydration reaction involving the following reactions:

and is carried out:

at a temperature comprised between 350 and 500° C., preferably comprised between 350 and 450° C. and more preferably comprised between 375 and 425° C.;

at a total pressure comprised between 0.2 and 2 MPa, preferably comprised between 0.2 and 1 MPa and more preferably comprised between 0.2 and 0.7 MPa;

and with a weight hourly space velocity (whsv), which is defined as being the ratio of the mass flow rate of alcohols (i.e. ethanol and isopropanol) to the mass of catalyst, comprised between 1 and 10 $h^{-1}$, preferably comprised between 2 and 8 $h^{-1}$.

The conversions of ethanol and isopropanol are advantageously greater than 90%, preferably greater than 95% and more preferably greater than 99%.

The conversions are calculated using the following formula:

$$\text{Alcohol conversion} = \left(1 - \frac{mC_{alcohol\ output}}{mC_{alcohol\ input}}\right) * 100 \text{ and with } mC_{alcohol} =$$

$$\text{Mass of alcohol} * \frac{\text{Molar mass of Carbon}}{\text{Molar mass of alcohol}}$$

It has been found that the catalysts utilized according to the invention also make it possible to achieve selectivities for the sought olefins (ethylene and propylene) greater than 95%, preferably greater than 99%.

The ethylene and propylene selectivities are calculated in carbon mass equivalent and with respect to the corresponding alcohol according to the formulae:

$$\text{Selectivity}_{ethylene} = \left(\frac{mC_{ethylene\ output}}{mC_{ethanol\ input} - mC_{ethanol\ output}}\right) * 100$$

and $$\text{Selectivity}_{propylene} = \left(\frac{mC_{propylene\ output}}{mC_{isopropanol\ input} - mC_{isopropanol\ output}}\right) * 100$$

The dehydration reaction is generally carried out in a unit comprising at least one isothermal or adiabatic reactor containing a bed, for example a fixed bed, of dehydration catalyst.

Preferably, the dehydration reaction is implemented in two adiabatic reactors in series, such as described in the document FR 2 978 146.

According to this preferred embodiment, the feedstock comprising the mixture of ethanol and isopropanol is mixed with a portion of the flow of recycled purified water and a portion of the flow of ethanol and isopropanol which have not been converted, originating from a purification zone. The mixture is introduced under pressure into a first gas/liquid exchanger in which said mixture undergoes an exchange of heat with the effluent originating from the last adiabatic reactor. The latent heat or enthalpy of condensation of the effluent originating from the last adiabatic reactor is used in order to vaporize the feedstock of alcohols in a mixture with the flow of recycled purified water and a flow of unconverted (non-dehydrated) ethanol/isopropanol, without the supply of external heat.

The feedstock of alcohols in a mixture with a flow of recycled purified water and a flow of unconverted (non-dehydrated) ethanol/isopropanol is then generally sent into a compressor.

Said vaporized and compressed mixture is then sent into a second single-phase gas-type exchanger, in which said mixture is heated using a heat exchanger with the effluent originating from the last adiabatic reactor. In said exchanger, for example of single-phase gas type, said vaporized and compressed feedstock is superheated and the effluent in the gaseous state, originating from the last adiabatic reactor is "desuperheated" without being condensed.

Said mixture of the feedstock and the two vaporized, compressed and heated flows in the single-phase gas-type exchanger is then heated, for example in a furnace, so as to make the inlet temperature in the first adiabatic dehydration reactor compatible with the temperature of the dehydration reaction. The effluent originating from the first reactor is sent into a second heating means before being introduced into the second adiabatic dehydration reactor.

The effluent originating from the second reactor then undergoes the two successive exchanges, described previously, in the exchangers.

The effluent after passing through the first exchanger is sent into a gas/liquid separation column where it is separated into an effluent comprising ethylene and propylene and an effluent comprising water. A portion of the effluent comprising water is optionally recycled, after cooling down, into the separation column.

The portion of the effluent comprising non-recycled water in the column is sent in a purification and separation stage. At least one flow of purified water and at least one flow of unconverted ethanol/isopropanol are then separated. A portion of said flow of unreacted ethanol/isopropanol originating from the purification stage is mixed with at least one portion of the flow of recycled purified water. The mixture of these two flows is carried out upstream of the first exchanger, with the aqueous feedstock of alcohols to be dehydrated.

The process according to the invention advantageously makes it possible to treat a mixture containing ethanol and isopropanol which originates from a so-called "IBE" fermentation unit. This IBE fermentation of sugars is in general carried out under strict anaerobiosis using microorganisms of the genus *Clostridium*. The fermentable sugars are preferably obtained after pre-treatment of a biomass of the lignocellulosic type and enzymatic hydrolysis. Lignocellulosic biomass represents one of the most abundant renewable resources on earth. The substrates considered are very varied, as they involve both the ligneous substrates (leafy and resinous), the by-products of agriculture (straw) or those of the industries that generate lignocellulosic waste (agri-food industries, paper mills).

The fermentation mash originating from the fermentation reactor undergoes a solid/liquid separation stage making it possible to separate an aqueous fermentation effluent (or "wine") containing the mixture of alcohols and a solid fraction. The "wine" originating from the IBE fermentation is an aqueous solution generally containing 15 to 45 g/L of alcohols, 2 to 30% by weight of which is ethanol, 10 to 60% by weight is isopropanol and 20 to 60% by weight is butanol.

In the specific case where the feedstock treated is an aqueous solution containing ethanol and isopropanol with more than 80% by weight of water with respect to the total weight of the aqueous solution, the process according to the invention comprises, before stage a) of dehydrating the ethanol and isopropanol, a stage of separating water from (or drying of) the aqueous solution. This stage can be carried out according to any technique known to a person skilled in the art.

For example according to a first embodiment, this separation consists of distillation in a column.

According to a second embodiment, the separation stage consists of a stage of solvent extraction using an aromatic cut comprising a mixture of aromatic compounds having 7 to 10 carbon atoms. Preferably, the aromatic cut comprises a mixture of 1,3,5-trimethylbenzene and 1,2,4-trimethylbenzene. This extraction is preferably carried out at a temperature comprised between 50 and 120° C. and preferably according to a counter-current extraction method. An aromatic cut containing the mixture of isopropanol, ethanol and optionally butanol and an aqueous fraction is extracted from the extraction column.

The aromatic cut containing the mixture of alcohols is then sent into a distillation unit the purpose of which is to separate the extraction solvent from the mixture of alcohols.

In the specific case where the mixture of alcohols also contains butanol, said mixture is treated in another separation unit, for example a distillation column, in order to separate the butanol and obtain an ethanol and isopropanol mixture with a low butanol content which is then treated in the ethanol and isopropanol dehydration unit.

Within the scope of the invention, the effluent originating from the partial drying stage can optionally contain acetone (for example between 0.3 and 1% by weight), which is a co-product of the "IBE" fermentation. Before the stage of separating the butanol from the ethanol-isopropanol mixture, the effluent is treated beforehand in a distillation unit operated in order to specifically separate the acetone from the mixture.

BRIEF DESCRIPTION OF FIGURES

Other features and advantages of the invention will be better understood and become clearly apparent on reading the description given hereafter with reference to the drawings in which.

Generally, similar elements are denoted by identical references in the figures.

Figure 1:
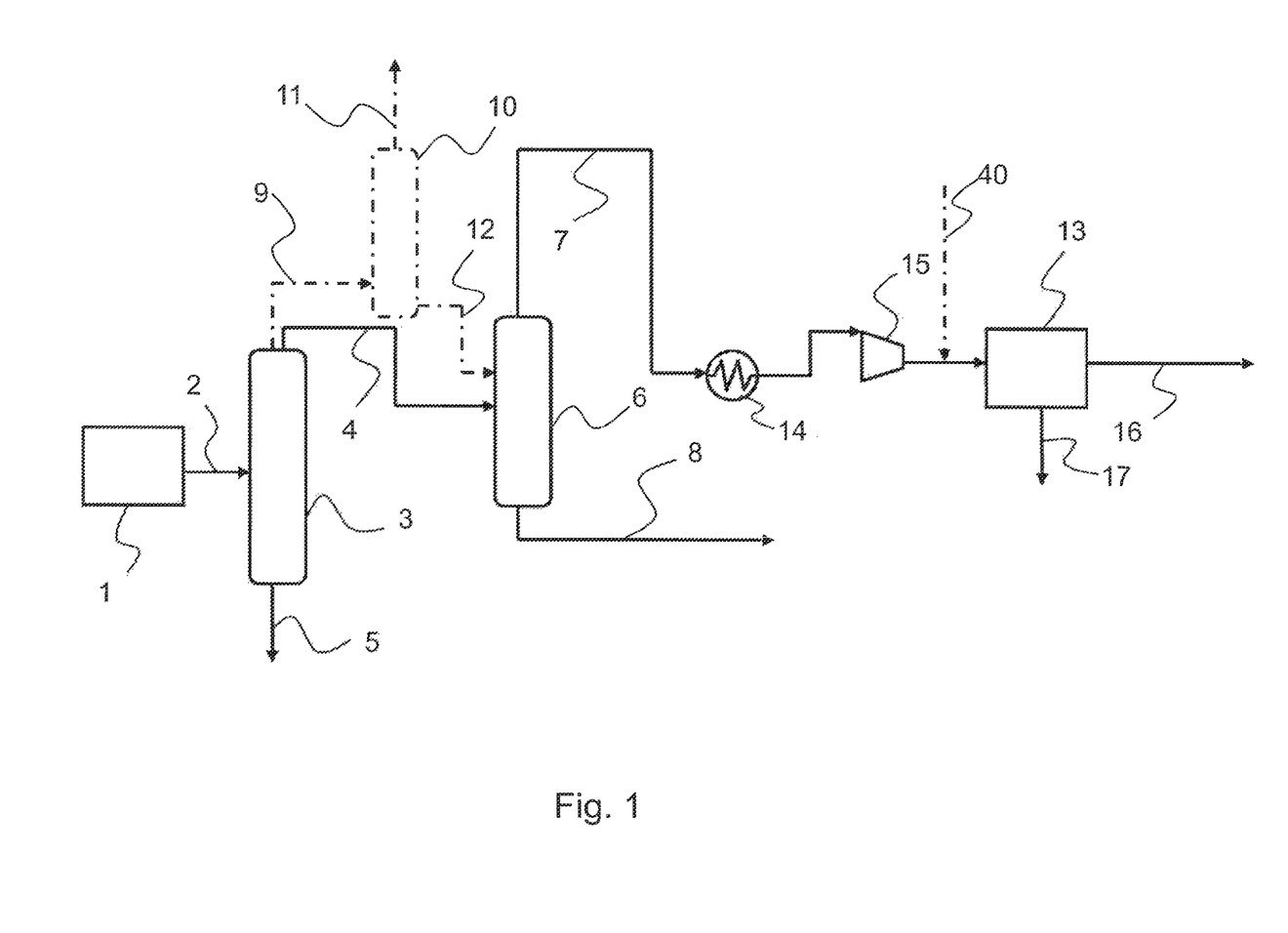
FIG. 1 diagrammatically shows a first embodiment of the process according to the invention.

With reference to FIG. 1, an aqueous effluent (or "wine") containing a mixture of ethanol, isopropanol and butanol, which originates from an "IBE" fermentation unit 1, is sent via the line 2 to a separation unit 3, which is a distillation column in the example of FIG. 1. The objective of this first stage, which can be described as "partial drying", is to reduce the water content of the IBE effluent (or wine) the composition of which depends not only on the origin of the sugars but also on the microorganisms utilized in the IBE fermentation.

The flow 2 entering the distillation column 3 can thus comprise up to 98% by weight of water.

With reference to FIG. 1, an aqueous fraction is extracted from the distillation column 3, which is removed at the bottom of the column via the line 5 and a fraction from the top containing an aqueous mixture of alcohols via the line 4. The aqueous mixture of alcohol typically has a content by mass of water with respect to the total weight of the aqueous mixture ranging up to 70% by weight. The distillation column 3 is designed and operated so as to preferably recover 99% by weight of the alcohols at the top of the column. For example a distillation column which treats an "IBE" mixture makes it possible for a fraction leaving the top to contain up to 65% by weight of a mixture of alcohols and at the bottom an aqueous fraction containing a few tens of ppm (by weight) of alcohols.

The aqueous mixture of ethanol, isopropanol and butanol is then sent into a distillation column 6 which is designed to carry out a separation of the butanol contained in the aqueous mixture of alcohols. Typically, the distillation column 6 is operated at a temperature comprised between 110 and 145° C. and at a pressure comprised between 0.4 and 0.7 MPa. Preferably, the distillation column is operated at a pressure of at least 0.5 MPa in order to maintain a temperature of at least 110° C. in the column in order to avoid the phenomena of liquid-liquid-vapour demixing.

When operated correctly, the distillation column makes it possible to recover, at the bottom of said column 6 via the line 8, a fraction containing 99% by weight of the butanol contained in the fraction introduced and, at the top via the line 7, at least 99% by weight of the isopropanol and ethanol contained in the fractions introduced.

According to an alternative embodiment also represented in FIG. 1, the mixture containing ethanol, isopropanol and butanol originating from the first, so-called "partial drying" stage is firstly sent via the line 9 into a distillation column 10 which is operated so as to extract the acetone. With reference to FIG. 1, the acetone is recovered at the top of the column 10 via the line 11 and the fraction containing the mixture of ethanol, isopropanol and butanol and depleted of acetone is recovered at the bottom of the column 10 and is sent via the line 12 into the distillation column 6.

With reference to FIG. 1, the mixture comprising water, isopropanol and ethanol extracted from the distillation column 6 is heated and vaporized using a heat exchanger 14 and then compressed using a compressor 15 before being sent to the dehydration stage, in the dehydration unit 13, in order to convert said alcohols to ethylene and propylene.

It should be noted that the effluent containing the mixture of isopropanol and ethanol originating from the distillation column 6 can be optionally sent into an adsorber (not shown) in order to further dry the effluent if necessary, before the dehydration stage so that the mixture of ethanol and isopropanol has a water content comprised between 30 and 75% by weight of water with respect to the total weight of the mixture.

The dehydration reaction is carried out in a dehydration unit comprising at least one reactor in which the ethanol and isopropanol are brought into contact with a catalyst capable of carrying out dehydration of the ethanol and isopropanol. In the case where the mixture of ethanol and isopropanol has a water content of less than 30% by weight with respect to the total weight of the mixture, the addition of water to said mixture is provided before dehydrating it. To this end it is provided, as indicated in FIG. 1, for a line 40 to be arranged upstream of the dehydration unit 13 allowing the injection of water into the mixture leaving the compressor 15. Preferably, the water is added in the form of vapour to the mixture of ethanol and isopropanol.

According to the invention, this stage of converting ethanol and isopropanol to olefins utilizes an alumina chosen from:

an alumina (A) having at least 50% by weight of γ alumina, a BET specific surface area measured according to the standard ASTM D 3663-03 comprised between 200 and 350 m$^2$/g, a mean mesopore diameter comprised between 5 and 15 nm, a sodium content of less than 50 ppm by weight and a sulphur content of less than 40 ppm by weight; and an alumina (B) having at least 50% by weight of γ alumina, a BET specific surface area measured according to the standard ASTM D 3663-03 comprised between 130 and 180 m$^2$/g, a mean mesopore diameter comprised between 14 and 20 nm, a sodium content comprised between 300 and 600 ppm by weight and a sulphur content comprised between 800 and 1300 ppm by weight;

It should be noted that the dehydration reaction in the presence of the catalyst according to the invention does not require thorough drying of the mixture of ethanol/isopropanol to the extent where its water content is comprised between 30 and 75% by weight with respect to the total weight of the mixture. The water contained in the mixture of alcohols is advantageously used in the dehydration process according to the invention as thermal fluid.

The catalytic dehydration reaction is carried out at a temperature comprised between 350 and 500° C., at a total pressure comprised between 0.2 and 2 MPa and with a weight hourly space velocity (whsv) defined as being the ratio of the mass flow rate of the mixture (ethanol and isopropanol) to the mass of catalyst comprised between 1 and 10 h$^{-1}$.

The dehydration stage is carried out in a unit which comprises one or more reactors arranged successively. The reactor(s) is (are) provided with the catalyst according to the invention, which is preferably in the form of extrudates and operate(s) either in a fixed bed or in a moving bed, but preferentially in a fixed bed.

The stage of dehydrating the alcohols is preferably implemented according to the process described in the patent application FR 2961202 which involves at least one adiabatic dehydration reactor. The process involves the effluent originating from the last dehydration reactor being sent to the heat exchanger and the feedstock to be dehydrated being introduced in a prior vaporization stage at a pressure less than the pressure of the effluent leaving the last dehydration reactor, so as to maximize the exchange of heat between the feedstock and the effluent originating from the last reactor, i.e. to exchange all of the enthalpy of vaporization of the feedstock and the enthalpy of condensation of said effluent.

At the end of the dehydration stage and after a distillation stage, a gaseous effluent 16 containing a mixture of propylene and ethylene is recovered at the outlet of the dehydration unit 13 and an effluent comprising water via the line 17. This gaseous effluent of propylene and ethylene can subsequently undergo a distillation stage with a view to separating the two olefins, which can then be upcycled as a raw material in petrochemistry.

As mentioned above the process according to the invention is advantageous from an economic point of view as it allows the production of ethylene and propylene from an aqueous mixture of isopropanol and ethanol by dispensing with a costly stage of separating the alcohols. Thanks to the process according to the invention, the ethanol and isopropanol are converted concomitantly in order to produce a flow of ethylene in a mixture with propylene which are olefins that can be easily separated in particular by distillation.

Figure 2:
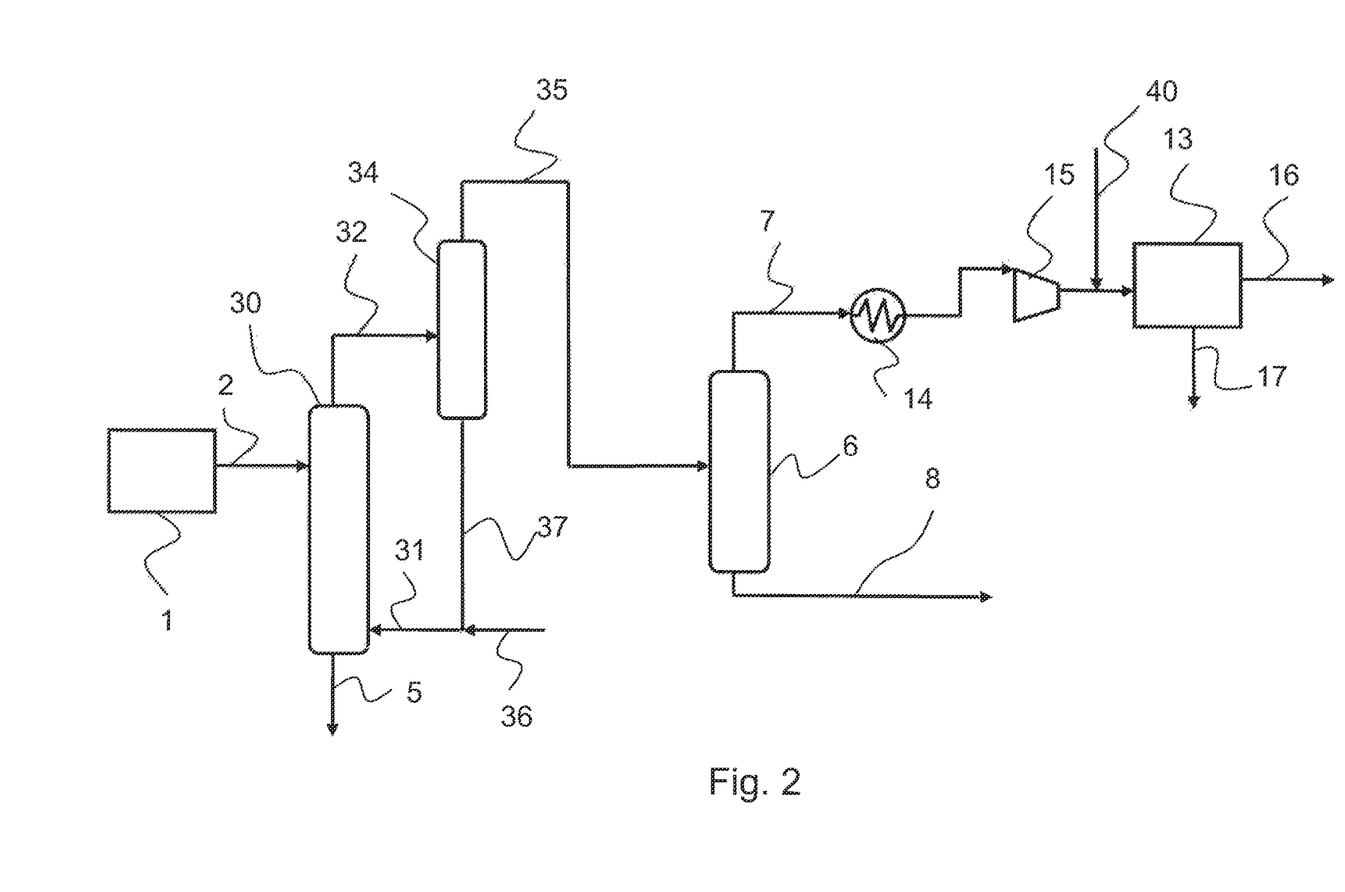
FIG. 2 diagrammatically shows a second embodiment of the process according to the invention.

FIG. 2 represents a second embodiment of the process according to the invention which differs from that of FIG. 1 in that the water separation unit is a solvent extraction unit comprising a liquid-liquid extraction column preferably completed by a distillation column.

With reference to FIG. 2, the fermentation liquor containing ethanol, isopropanol and butanol, originating from the IBE fermentation unit 1 is sent via the line 2 into a liquid-liquid extraction column 30 and into which a solvent which is an aromatic cut comprising a mixture of aromatic compounds having 7 to 10 carbon atoms is injected, via the line 31, preferably in counter-current, for example at the bottom of the extraction column 30. The solvent according to the invention has the ability to absorb ethanol, isopropanol and butanol and moreover is virtually insoluble in water. For example the solvent is a heavy reformate originating from a catalytic reforming unit for gasolines which treats a naphtha cut from crude oil in order to increase the aromatic compounds content. This stage of catalytic reforming (aromatization of gasoline) makes this gasoline heavier. Also, in order to guarantee a final boiling point of the gasoline in accordance with the commercial specification, it is usual to redistill these gasolines in order to remove the heaviest fraction which is called "heavy reformate".

By means of the difference in density and thanks to the affinity of the solvent vis-à-vis ethanol, isopropanol and butanol, an organic effluent 32 containing the aromatic cut and the sought alcohols are recovered at the top of the extraction column and a flow of water is recovered at the bottom, via the line 5. In order to implement the liquid-liquid extraction, the weight ratio between the feedstock and the solvent is generally comprised between 0.5 and 5. The bringing into contact with the solvent is generally carried out at a temperature comprised between 60 and 120° C. and at a pressure comprised between 0.5 and 5 MPa. As shown in FIG. 2, a line 36 makes it possible to top up with solvent if this is necessary for the operation of the column 30.

Thus, an effluent containing at least 99% by weight of the alcohols present in the mixture of alcohols is recovered at the top of the liquid-liquid extraction column.

According to FIG. 2, the organic effluent extracted at the top of the liquid-liquid extraction column 30 is sent via the line 32 into a distillation column 34 configured in order to separate, at the top, the mixture comprising ethanol, isopropanol and butanol from the extraction solvent which is drawn off at the bottom of said distillation column 34. The solvent which is recovered from the distillation column via the line 37 is recycled via the line 31 into the liquid-liquid extraction column 30. This distillation is preferably carried out at reduced pressure, preferably comprised between 0.02 and 0.05 MPa in order to reduce the temperature at the bottom of the column and thus be able to use a "low pressure" vapour as a reboiling fluid. The process according to the embodiment in FIG. 2 has the advantage of consuming less energy with respect to the first embodiment as, unlike a distillation, the utilization of the liquid-liquid extraction column does not require the mixture of alcohols to be vigorously heated in order to dry it.

In the embodiment of FIG. 2, the organic effluent drawn off via the line 35 and essentially constituted by ethanol, isopropanol and butanol is sent into a butanol separation unit 6. The separation unit 6, for example a distillation column, is operated in order to provide a mixture essentially constituted by ethanol and isopropanol which is drawn off via the line 7 and an effluent essentially constituted by butanol which is drawn off via the line 8.

With reference to FIG. 2, the mixture 7 essentially constituted by ethanol and isopropanol is heated by the heat exchanger 14 then compressed by the compressor 15 before being sent with water supplied via the line 40 into the dehydration unit 13. The supply of make-up water, via the line 40, makes it possible to regulate the water content of the feedstock of alcohols so as to provide an ethanol-isopropanol-water mixture the water content of which is comprised between 30 and 75% by weight of water with respect to the total weight of the mixture.

Figure 3:
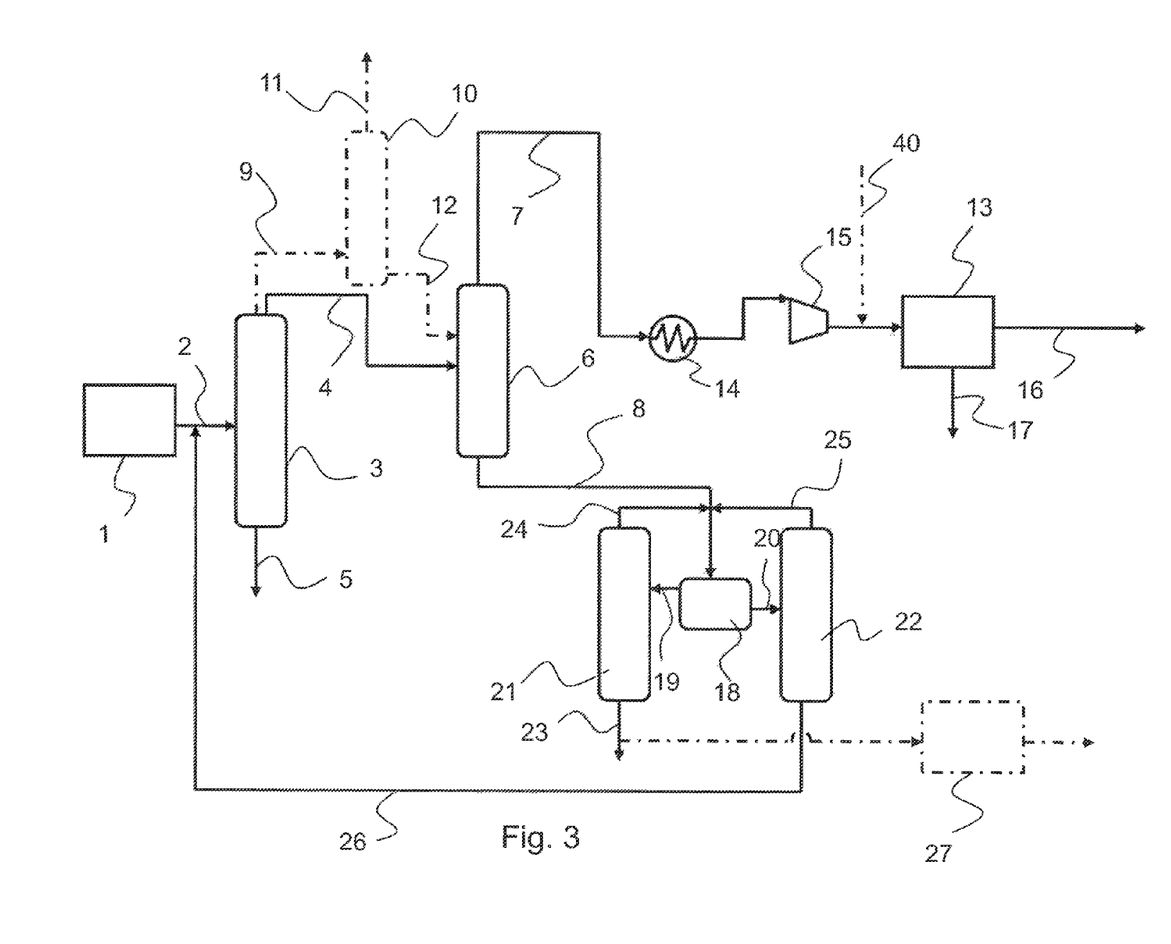
FIG. 3 shows another embodiment of FIG. 1 also comprising a butanol purification stage.

FIG. 3 shows an embodiment complementary to that of FIG. 1. As indicated in FIG. 3, the aqueous flow of butanol 8 which is extracted at the bottom of the distillation column 6 is treated in a separation unit in order to recover the butanol. To this end, the aqueous flow of butanol is cooled down, for example to a temperature of 60° C. in a flask 18 in order to demix the mixture into two phases namely an organic phase essentially containing butanol (for example at least 70% by weight of butanol) and an aqueous phase.

The two phases are treated in a hetero-azeotropic distillation system which comprises two columns 21, 22 operating in parallel. The organic phase mainly containing butanol is sent via the line 19 into the hetero-azeotropic distillation column 21 which preferably operates at a pressure comprised between 0.3 and 10 MPa and at a temperature comprised between 115 and 150° C. in order to avoid problems of liquid-liquid-vapour demixing. An effluent having a content by weight of at least 99% butanol is drawn off at the bottom of said column 21 via the line 23 and an aqueous effluent is drawn off at the top, via the line 24, which is sent into the separator tank 18.

The aqueous phase still containing butanol, which is drawn off from the two-phase separator tank 18, is sent via the line 20 into the hetero-azeotropic distillation column 22. Respectively, a flow rich in water is recovered at the bottom of said column 22 and an effluent is recovered at the top, which is recycled, via the line 25, into the two-phase separator tank 18. The column 22 is operated under less severe conditions, for example at a pressure less than that of the column 21.

Advantageously, all or part of the butanol which is recovered from the hetero-azeotropic distillation unit is sent into a butanol catalytic dehydration unit 27 with a view to its conversion to butene and preferably to 2-butene.

According to an advantageous embodiment (not shown), the 2-butene thus produced is reacted with ethylene in a reactor in order to form propylene by means of a metathesis reaction, known to a person skilled in the art.

EXAMPLES

Different catalysts were tested for the dehydration of a mixture containing 25% by weight of ethanol, 25% by weight of isopropanol and 50% by weight of water with respect to the total weight of the mixture. The catalysts are in the form of trilobed extrudates with a diameter of 1.6 mm.

Table 1 below gives the characteristics of the catalysts tested.

TABLE 1

| Catalyst | Type of alumina | Mean mesopore diameter (nm) | Specific surface area (m²/g) measured according to ASTM D 3663-03 | Sodium content (ppm by weight) | Sulphur content (ppm by weight) |
|---|---|---|---|---|---|
| C1 (according to the invention) | Pseudo-cubic γ alumina | 10.3 | 208 | Less than 20 | Less than 40 |
| C2 (according to the invention) | Cubic γ alumina | 8.5 | 216 | 28 | Less than 40 |
| C3 (according to the invention) | Cubic γ alumina | 7.4 | 232 | 35 | Less than 40 |
| C4 (comparative) | Cubic γ alumina and χ alumina | 5.7 | 155 | 417 | Less than 40 |
| C5 (comparative) | Cubic γ alumina | 8.7 | 270 | 394 | 1262 |
| C6 (according to the invention) | Cubic γ alumina | 15.7 | 175 | 550 | 903 |
| C7 (according to the invention) | tetragonal γ alumina + θ alumina | 18.3 | 152 | 448 | 1210 |
| C8 (comparative) | δ alumina and χ alumina | 25.8 | 154 | 401 | Less than 40 |
| C9 (comparative) | Cubic γ alumina | 18.3 | 143 | 222 | 1121 |

The catalysts C1, C2 and C3 are consistent with an alumina (A) according to the invention and the catalysts C6 and C7 are consistent with an alumina (B) according to the invention.

Catalyst C4 is not consistent with an alumina (A) according to the invention as its specific surface area and its sodium content are outside the claimed ranges. Moreover, catalyst D is not consistent with an alumina (B) according to the invention as its mean mesopore diameter is outside the range 14-20 nm.

Catalyst C5 which does not conform is distinguished from an alumina (A) according to the invention by the sodium and sulphur contents which are higher than the upper limit of the claimed ranges. Catalyst C5 which also is not consistent with an alumina (B) according to the invention and is distinguished by its mean mesopore diameter and its specific surface area.

Catalyst C8 does not correspond to the definition of an alumina (A) according to the invention as the mean mesopore diameter, the specific surface area and the sodium content are outside the claimed ranges. Moreover, catalyst C8 is not consistent with an alumina (B) according to the invention as it has a mean mesopore diameter greater than the claimed range and a sulphur content of less than 800 ppm by weight Catalyst C9 is not consistent with an alumina (A) according to the invention because of its mean mesopore diameter, its specific surface area, its sodium and sulphur content. Catalyst I is distinguished from an alumina (B) according to the invention by its sodium content.

Before their utilization in the dehydration test of the mixture of alcohols, all the catalysts have undergone a conditioning phase which comprises the following stages:

i) heating the catalyst from ambient temperature to 550° C. under a flow of air at 5 Nl/h with a temperature gradient of 20° C. per hour;

ii) maintaining a temperature of 550° C. under a flow of air for 2 hours;

iii) cooling the catalyst to the temperature of the test under a flow of nitrogen at 100 Nl/h;

iv) maintaining the catalyst at the temperature of the test under a flow of nitrogen at 100 Nl/h for 5 hours.

The dehydration reaction is carried out in an isothermal reactor containing a fixed bed of dehydration catalyst. All the catalysts were tested under the same operating conditions namely:

temperature in the reactor=375° C.;
relative pressure in the reactor=0.2 MPa;
weight hourly space velocity (whsv), which is defined as being the ratio of the mass flow of (ethanol+isopropanol) to the mass of catalyst=2 $h^{-1}$.

The effluent leaving the dehydration reactor is sent into a high pressure (HP) separator in order to separate a first gaseous flow and a liquid flow. The liquid flow is then transferred into a low pressure (LP) separator where a second gaseous flow and a second liquid flow is separated. The two gaseous flows are mixed before being analyzed.

The liquid and gaseous flows are analyzed by gas chromatography.

Table 2 gives the catalytic performances of the tested aluminas after testing for 72 hours.

The conversions and the selectivities were calculated from the formulae described above.

Finally, the purity of the C2 cut is calculated with respect to the ethylene, ethane and methane whereas the purity of the C3 cut is calculated with respect to the propylene, propane and cyclopropane. Thus the ethylene purity of the C2 cut and the propylene purity of the C3 cut are expressed as follows:

$$\text{Ethylene purity} = \left( \frac{mC_{ethylene\ output}}{mC_{ethylene\ output} + mC_{ethane\ output} + mC_{methane\ output}} \right) * 100$$

$$\text{Propylene purity} = \left( \frac{mC_{propylene\ output}}{mC_{propylene\ output} + mC_{propane\ output} + mC_{cyclopropane\ output}} \right) * 100$$

TABLE 2

| | Catalyst | | | | | | | | |
|---|---|---|---|---|---|---|---|---|---|
| | C1 | C2 | C3 | C4 | C5 | C6 | C7 | C8 | C9 |
| Conversion of iso-Propanol (%) | 100 | 100 | 100 | 100 | 100 | 100 | 100 | 99.90 | 100 |

TABLE 2-continued

| | Catalyst | | | | | | | | |
|---|---|---|---|---|---|---|---|---|---|
| | C1 | C2 | C3 | C4 | C5 | C6 | C7 | C8 | C9 |
| Propylene Selectivity | 99.88 | 99.92 | 99.81 | 99.56 | 99.62 | 99.62 | 99.85 | 98.48 | 98.39 |
| Dipropylether Selectivity | 0 | 0 | 0 | 0 | 0 | 0 | 0 | 0.15 | 0 |
| Propane Selectivity | 0.07 | 0.03 | 0.09 | 0.20 | 0.21 | 0.12 | 0.07 | 0.06 | 0.96 |
| Propanal Selectivity | 0.04 | 0.05 | 0.10 | 0.15 | 0.10 | 0.24 | 0.06 | 0.12 | 0.60 |
| Ethoxypropane Selectivity | 0.01 | 0 | 0 | 0 | 0 | 0 | 0 | 0 | 0 |
| C3 cut composition (% by weight) | | | | | | | | | |
| Propylene | 99.93 | 99.97 | 99.91 | 99.80 | 99.79 | 99.88 | 99.93 | 99.93 | 99.03 |
| Propane | 0.07 | 0.03 | 0.09 | 0.2 | 0.21 | 0.12 | 0.07 | 0.07 | 0.97 |
| Cyclopropane | 0 | 0 | 0 | 0 | 0 | 0 | 0 | 0 | 0 |
| Ethanol conversion (%) | 92.02 | 97.16 | 97.60 | 83.00 | 86.20 | 90.80 | 91.68 | 59.48 | 89.50 |
| Methane Selectivity | 0.00 | 0.00 | 0.00 | 0.00 | 0.00 | 0.00 | 0.00 | 0.00 | 0.00 |
| Ethylene Selectivity | 98.96 | 99.65 | 99.65 | 97.84 | 98.17 | 98.70 | 98.97 | 81.82 | 96.84 |
| Ethane Selectivity | 0.16 | 0.10 | 0.13 | 0.23 | 0.26 | 0.19 | 0.09 | 0.18 | 1.10 |
| Diethylether Selectivity | 0.54 | 0.16 | 0.12 | 1.45 | 1.10 | 0.75 | 0.64 | 16.10 | 0.71 |
| EthylPropylEther Selectivity | 0.03 | 0 | 0 | 0.12 | 0.09 | 0.08 | 0.05 | 1.70 | 0.09 |
| Butane Selectivity | 0.17 | 0.13 | 0.16 | 0.22 | 0.17 | 0.11 | 0.13 | 0.15 | 0.49 |
| Butene Selectivity | 0.08 | 0.04 | 0.10 | 0.11 | 0.16 | 0.12 | 0.10 | 0.04 | 0.65 |
| C5+ Selectivity | 0.02 | 0.01 | 0.01 | 0.03 | 0.05 | 0.05 | 0.02 | 0.01 | 0.12 |
| C2 cut composition (% by weight) | | | | | | | | | |
| Ethylene | 99.84 | 99.90 | 99.87 | 99.77 | 99.74 | 99.81 | 99.91 | 99.78 | 98.88 |
| Ethane | 0.16 | 0.10 | 0.13 | 0.23 | 0.26 | 0.19 | 0.09 | 0.22 | 1.12 |
| Methane | 0.00 | 0.00 | 0.00 | 0.00 | 0.00 | 0.00 | 0.00 | 0.00 | 0.00 |

The utilization of the catalysts according to the invention (C1, C2, C3, C6 and C7) makes it possible to obtain excellent isopropanol conversion rates but also ethanol conversion rates which are respectively 100% and of the order of 90%. On the other hand, it is noted that with the catalysts not according to the invention (D, E, H, I) the ethanol conversion rates are less than 90%.

Moreover it is observed that the purity of the propylene in a C3 cut and that of the ethylene in a C2 cut are better when the catalysts according to the invention are utilized. The C2 and C3 cuts thus produced are of polymer grade and can therefore be used in the petrochemical industry in particular for the manufacture of polymers.

The invention claimed is:

1. A process for production of a mixture of ethylene and propylene from a mixture containing ethanol, isopropanol and water having a water content comprised between 30 and 75% by weight with respect to the total weight of the mixture, said process comprising:
   a) bringing the mixture of ethanol, isopropanol, and water into contact, in a dehydration unit, with a dehydration catalyst chosen from:
      an alumina (A) having a BET specific surface area measured according to the standard ASTM D 3663-03 of between 200 and 280 $m^2/g$, a mean mesopore diameter of between 5 and 15 nm, a sodium content of less than 50 ppm by weight, and a sulfur content of less than 40 ppm by weight; and
      an alumina (B) having a BET specific surface area measured according to the standard ASTM D 3663-03 of between 130 and 180 $m^2/g$, a mean mesopore diameter of between 14 and 20 nm, a sodium content of between 300 and 600 ppm by weight, and a sulfur content of between 800 and 1300 ppm by weight,
   wherein the bringing into contact is carried out at a temperature of between 350 and 500° C., at a total pressure of between 0.2 and 2 MPa, and with a weight hourly space velocity, defined as being the ratio of the mass flow rate of ethanol and isopropanol to the mass of catalyst, of between 1 and 10 $h^{-1}$; and
   b) withdrawing an effluent containing ethylene and propylene from said dehydration unit.

2. The process according to claim 1, wherein the mixture of ethanol, isopropanol, and water contains between 1 and 75% by weight of ethanol and between 99 and 25% by weight of isopropanol with respect to the total weight of ethanol and isopropanol.

3. The process according to claim 1, wherein aluminas (A) and (B) are gamma aluminas.

4. The process according to claim 1, wherein said dehydration catalyst is alumina (A) having a mean mesopore diameter between 6 and 12 nm.

5. The process according to claim 1, wherein said dehydration catalyst is alumina (B) having a BET specific surface area measured according to the standard ASTM D 3663-03 between 150 and 180 $m^2/g$.

6. The process according to claim 1, wherein said dehydration catalyst is alumina (B) having a mean mesopore diameter between 15 and 20 nm.

7. The process according to claim 1, wherein prior to stage a) the mixture of ethanol, isopropanol, and water also comprises butanol, and prior to stage a said mixture of ethanol, isopropanol, and water is treated to remove butanol.

8. The process according to claim 7, wherein removal of butanol is carried out by distillation.

9. The process according to claim 1, wherein, before stage a), the mixture of ethanol, isopropanol, and water is brought into contact with an aromatic cut comprising a mixture of aromatic compounds having 7 to 10 carbon atoms in a separation unit comprising a liquid-liquid extraction column (30), so as to separate from said extraction column (30) an aqueous fraction (5) and an organic fraction containing the aromatic cut, ethanol and isopropanol, said organic fraction is sent into a distillation column (34) and an effluent (37) containing the aromatic cut and a mixture (35) containing ethanol and isopropanol are removed from said distillation column (34), and said mixture containing ethanol and isopropanol is sent into the dehydration unit of stage a).

10. The process according to claim 9, wherein, the aromatic cut is a mixture of 1,3,5-trimethylbenzene and 1,2,4-trimethylbenzene.

11. The process according to claim 9, wherein, the mixture of ethanol, isopropanol and water is brought into contact with the aromatic cut in counter-current.

12. The process according to claim 1, wherein, before stage a) the mixture of ethanol, isopropanol and water is sent into a separation unit comprising a distillation column (3) so as to separate an aqueous fraction and an effluent containing a mixture of ethanol, isopropanol and water with a water content comprised between 30 and 75% by weight with respect to the total weight of the mixture of ethanol, isopropanol and water and the effluent is sent into the dehydration unit of stage a).

13. The process according to claim 1, wherein the mixture of ethanol, isopropanol, and water originates from an Isopropanol-Butanol-Ethanol fermentation unit.

14. The process according to claim 1, wherein the bringing into contact of stage a) is carried out in at least one reactor at a temperature of between 350 and 450° C., at a total pressure of between 0.2 and 2 MPa, and with a weight hourly space velocity of between 1 and 10h$^{-1}$.

15. The process according to claim 1, wherein stage a) is carried out in two adiabatic reactors in series.

16. The process according to claim 1, wherein said dehydration catalyst is alumina (A) having a mean mesopore diameter between 7 and 11 nm.

17. The process according to claim 14, wherein the bringing into contact of stage a) is carried out at a temperature of between 375 and 425° C.

18. The process according to claim 14, wherein the bringing into contact of stage a) is carried out at a total pressure of between 0.2 and 1 MPa.

19. The process according to claim 14, wherein the bringing into contact of stage a) is carried out at a weight hourly space velocity of 2 and 8 h$^{-1}$.

20. The process according to claim 1, wherein said dehydration catalyst is said alumina (A) having a BET specific surface area measured according to the standard ASTM D 3663-03 of between 200 and 280 m$^2$/g, a mean mesopore diameter of between 5 and 15 nm, a sodium content of less than 50 ppm by weight, and a sulfur content of less than 40 ppm by weight.

21. The process according to claim 1, wherein said dehydration catalyst is said alumina (B) having a BET specific surface area measured according to the standard ASTM D 3663-03 of between 130 and 180 m$^2$/g, a mean mesopore diameter of between 14 and 20 nm, a sodium content of between 300 and 600 ppm by weight, and a sulfur content of between 800 and 1300 ppm by weight.

22. The process according to claim 20, wherein said alumina (A) has a BET specific surface area measured according to the standard ASTM D 3663-03 of between 200 and 230 m$^2$/g, and a mean mesopore diameter of between 7 and 11 nm.

* * * * *